United States Patent [19]
DeVane

[11] Patent Number: 6,138,677
[45] Date of Patent: Oct. 31, 2000

[54] APPARATUS AND METHOD FOR CONSTRAINING A PRISONER IN A SEATED POSITION

[76] Inventor: Billy DeVane, 459 E. University Ave., Orange City, Fla. 32763

[21] Appl. No.: 09/192,143

[22] Filed: Nov. 14, 1998

[51] Int. Cl.⁷ .................................................. A61B 19/00
[52] U.S. Cl. ........................................... 128/869; 128/876
[58] Field of Search ..................................... 128/845, 846, 128/869–879; 602/5, 12; 70/14–16

[56] References Cited

U.S. PATENT DOCUMENTS

| | | | |
|---|---|---|---|
| 2,295,806 | 9/1942 | Peterson | 128/878 |
| 4,004,583 | 1/1977 | Johnson | 128/876 |
| 5,172,703 | 12/1992 | Tiede | 128/875 |
| 5,345,947 | 9/1994 | Fisher . | |
| 5,469,813 | 11/1995 | Peden . | |
| 5,542,433 | 8/1996 | Saupe . | |
| 5,581,853 | 12/1996 | Miller et al. . | |
| 5,651,375 | 7/1997 | Cunningham . | |

*Primary Examiner*—Michael A. Brown
*Attorney, Agent, or Firm*—Paul S. Rooy

[57] ABSTRACT

An apparatus and method for constraining a prisoner in a seated position. The apparatus comprises a belt removably attached to a hobble. The belt comprises a belt D-ring and a belt alligator clip attached to a belt strap. The hobble comprises a snap hook attached to one extreme of a hobble strap, and a hobble alligator clip attached to an opposite extreme of the hobble strap. The method includes the steps of placing a prisoner on his side, tightening the hobble around his ankles, tightening the belt around his waist, attaching the hobble to the belt by passing the extreme of the hobble strap through the belt D-ring and attaching the snap hook to the hobble alligator clip, and leaving the prisoner seated on a surface with his legs resting on the surface in front of him.

10 Claims, 3 Drawing Sheets

APPARATUS AND METHOD FOR CONSTRAINING A PRISONER IN A SEATED POSITION

BACKGROUND OF THE INVENTION

1. Field of the Invention

This invention relates to prisoner restraints, and in particular to an apparatus and method for constraining a prisoner in a seated position.

2. Background of the Invention

A problem of long standing associated with prisoner restraint is a method and apparatus to constrain a prisoner's hands and feet which will prevent a prisoner from using his feet as weapons. The need for a method which is not only safe for the arresting officer as well as for the prisoner has recently become apparent. This problem is especially pronounced where a prisoner is aggressive and combative, and/or under the influence of a drug such as cocaine, PCP or methamphetamines, which may have the effect of actually quadrupling or quintupling the user's physical strength.

A number of methods have been employed in the past to restrain prisoners. One such method is known as "hog-tying." This method positions the prisoner on his stomach, with his hands in handcuffs. A hobble is placed around the prisoner's ankles, and a line attaches the hobble to the handcuffs. In this position, the subject's feet and hands are bound together, helping prevent the prisoner from hurting others by kicking them.

The hog-tying method has been banned recently by a number of jurisdictions, because of cases where the prisoner has died from inability to breathe properly ("positional asphyxia"). Recent law suits filed in the wake of such unfortunate prisoner deaths have resulted in awards in the tens of millions of dollars. Thus the problem of finding an effective and safe replacement for the hog-tying method is acute and pressing.

Another prisoner restraint method used has been the "slam dunk." In this method, the subject is placed stomach down on the ground, and a peace officer kneels on the prisoner's back. This method has also been known to cause positional asphyxia.

A third method used to subdue prisoners to prevent them from damaging themselves or officers is the lateral vascular neck restraint, also known as the "choke hold." This method involves the officer placing an arm around the prisoner's neck and squeezing. If performed properly, the lateral vascular neck restraint will interrupt the flow of blood to the prisoner's head during a period of four (4) seconds, which effectively renders the prisoner passive. Unfortunately, if performed incorrectly, the choke hold can hurt or even kill the prisoner. This method has also lead to numerous multi-million dollar awards, and has been banned in a number of jurisdictions.

Thus the problem remains: what apparatus and method may be used to effectively constrain a prisoner's feet, which apparatus and method will not simultaneously subject the prisoner or the arresting officer(s) to unnecessary danger. The apparatus should be easily transported in a police vehicle and be transportable by a single officer from a police vehicle to a field incident, and the method must be practicable on an aggressive/combative subject by as few as two officers. In addition, the apparatus and method should provide that the subject's legs will be secured so as to prevent the subject from kicking or otherwise using his legs to resist the officer's controlling effort. Finally, the apparatus must be composed of heavy duty materials which require little or no maintenance.

Existing Designs

One apparatus which has been proposed to use to constrain a prisoner is taught in U.S. Pat. No. 5,542,433, which was granted to Saupe for a Leg to Waist Prisoner Restraint, While this apparatus taught a means of attaching a hobble to a waist band, the method disclosed involved using the now-banned hog-tying restraint with attendant prisoner health hazards. In addition, the hobble is taught to be permanently attached to the belt, thus requiring that the entire apparatus be purchased, which would lead to unnecessary expense where only the hobble portion is required. Finally, the apparatus itself presents a confusingly Medusa-like snarl of straps, which could lead to officer confusion in its use, especially at night with a belligerent and combative prisoner.

U.S. Pat. Nos. 5,469,813 and 5,345,947 were granted Peden and Fisher respectively for prisoner restraints. Both these patents taught use of the apparatuses to constrain prisoners in essentially the "hog-tied" position, which could lead to the prisoner-harm-and-consequet-lawsuit problems mentioned previously. In addition, neither of these references teach a hobble which incorporates a hobble alligator clip to securely hold the prisoner's feet together. Such omission could lead to the prisoner's feet becoming fee, and possible harm to the arresting officers and the prisoner himself.

SUMMARY OF THE INVENTION

Accordingly, it is an object of the present invention to provide an apparatus and method for constraining a prisoner in a seated position which is not conducive to positional asphyxia. Design features allowing this object to be accomplished include a belt removably attached to a hobble by means of a hobble strap. Advantages associated with the accomplishment of this object include reduced risk to prisoners, as well as reduced lawsuits against police agencies and governments as a result of prisoners harmed by positional asphyxia. Still another advantage of the instant apparatus and method is the ability to use same while transporting a prisoner in a vehicle in a conventional, upright seated posture. This prevents the hog-tying problem of a prisoner rolling off the rear seat of a police car and becoming wedged on the floor, stomach down, between the front and rear seats of the car, with his diaphragm pressing against the drive-shaft hump, a position which has caused asphyxia.

It is another object of the present invention to provide an apparatus and method for constraining a prisoner in a seated position which is simple to use. Design features allowing this object to be accomplished include a belt comprising a belt D-ring and a belt alligator clip attached to a belt strap, and a hobble attached to the belt by means of a hobble strap through the belt D-ring. Benefits associated with the accomplishment of this object include ease of use and quick learning of the method, and the ability of one or two officers to subdue even violent subjects using the instant method and apparatus.

It is still another object of this invention to provide an apparatus and method for constraining a prisoner in a seated position which prevents a prisoner from kicking out. Design features enabling the accomplishment of this object include a belt around the prisoner's waist, a hobble around the prisoner's feet, and a hobble strap connecting the belt to the hobble. An advantage associated with the realization of this object is reduced chance of harm to the prisoner and those around him.

It is another object of the present invention to provide an apparatus and method for constraining a prisoner in a seated position which permits the hobble to be used by itself, without a belt attached. Design features allowing this object to be accomplished include a hobble removably attached to a belt. Benefits associated with the accomplishment of this object include elimination of the need for a police agency to purchase and stock any more belts than are required, along with the associated cost savings.

It is still another object of this invention to provide an apparatus and method for constraining a prisoner in a seated position where the apparatus is made of materials which are durable, maintenance-free, and easy to wash and disinfect. Design features enabling the accomplishment of this object include a belt and hobble made of strong synthetic material, and hardware made of brass or similar durable material. Advantages associated with the realization of this object include reduced maintenance cost and the ability to easily clean the apparatus as opposed to buying new, along with associated cost savings.

NOTHING CONTAINED IN THIS DISCLOSURE IS INTENDED TO BE A WARRANTY OR GUARANTEE, EXPRESS OR IMPLIED, REGARDING THE SAFETY OF A PRISONER CONSTRAINED USING THE INSTANT INVENTION.

BRIEF DESCRIPTION OF THE DRAWINGS

The invention, together with the other objects, features, aspects and advantages thereof will be more clearly understood from the following in conjunction with the accompanying drawings.

Three sheets of drawings are provided. Sheet one contains FIG. 1. Sheet two contains FIGS. 2 and 3. Sheet three contains FIGS. 4 and 5.

DETAILED DESCRIPTION OF THE PREFERRED EMBODIMENT

Figure 1:
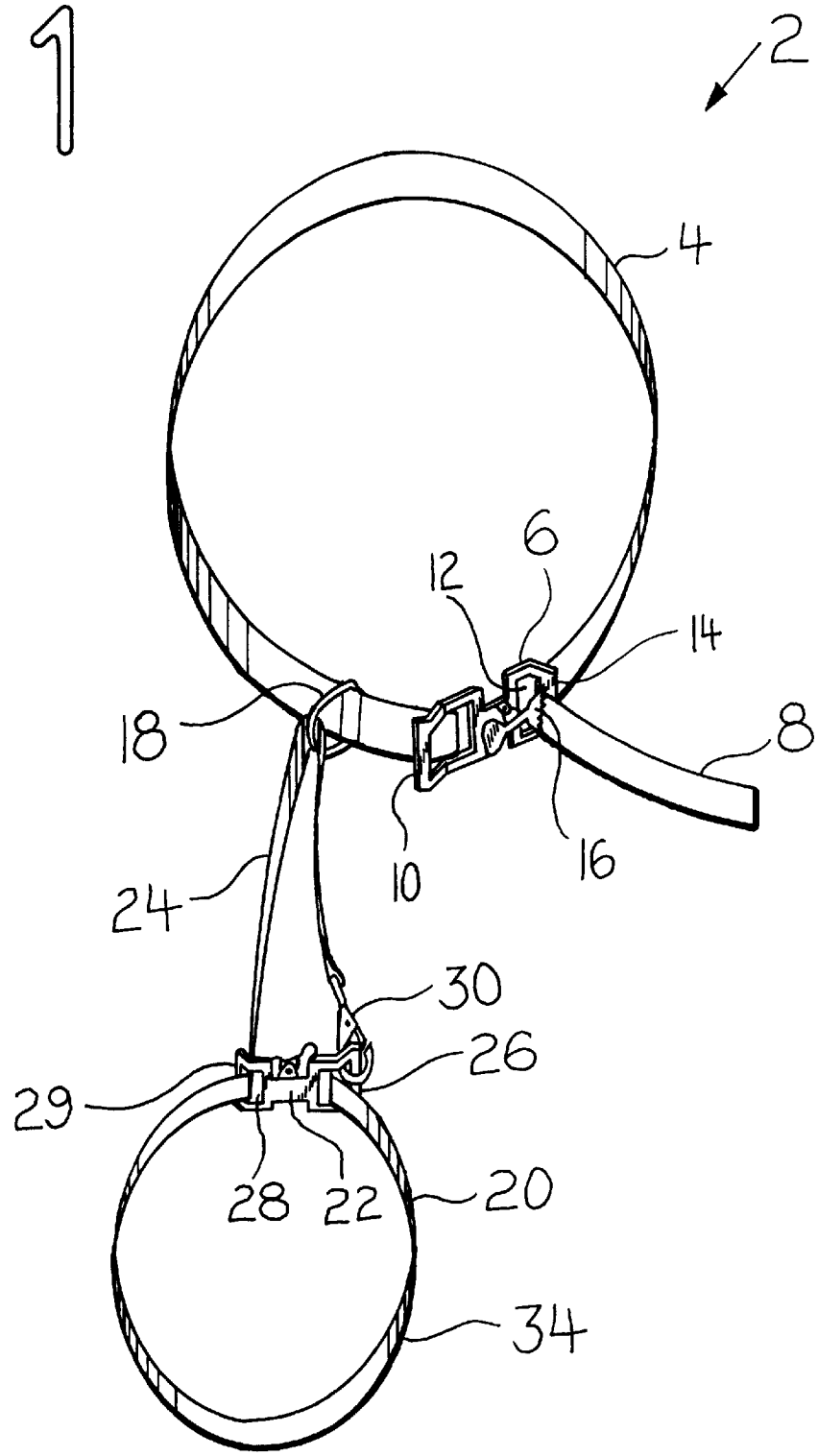
FIG. 1 is a front isometric view of an apparatus and method for constraining a prisoner in a seated position.
Figure 2:
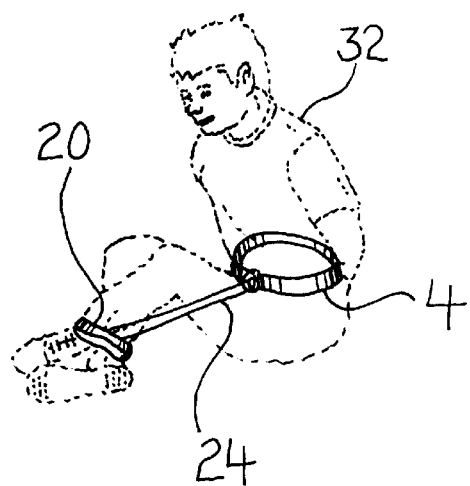
FIG. 2 is a side isometric view of a prisoner being constrained by means of the instant apparatus and method for constraining a prisoner in a seated position.
Figure 3:
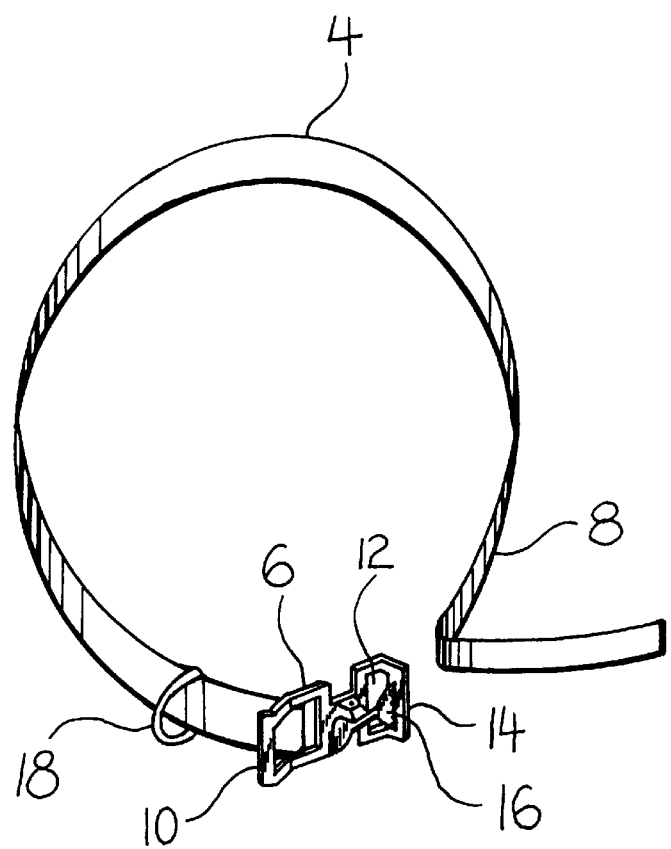
FIG. 3 is a front isometric view of a belt.

FIG. 1 is a front isometric view of apparatus for constraining a prisoner in a seated position 2, which comprises belt 4 and hobble 20. Referring now also to FIG. 3, belt 4 comprises belt alligator clip 6 and belt D-ring 18 attached to belt strap 8. Belt alligator clip 6 comprises belt alligator clip mouth 12, belt alligator clip back bar 10, and belt alligator clip mouth bar 14, against which spring-loaded teeth 16 press. When belt strap 8 is threaded through belt alligator clip mouth 12 as is illustrated in FIG. 1, spring-loaded teeth 16 clamp down on belt strap 8 and hold it in place against belt alligator clip mouth bar 14. Thus, when belt 4 is placed around the waist of a prisoner 32 as is illustrated in FIG. 2, the action of threading belt strap 8 through belt alligator clip mouth 12 and pulling on that portion of belt strap 8 which protrudes through belt alligator clip mouth 12 tightens belt 4 around the waist of prisoner 32.

Figure 4:
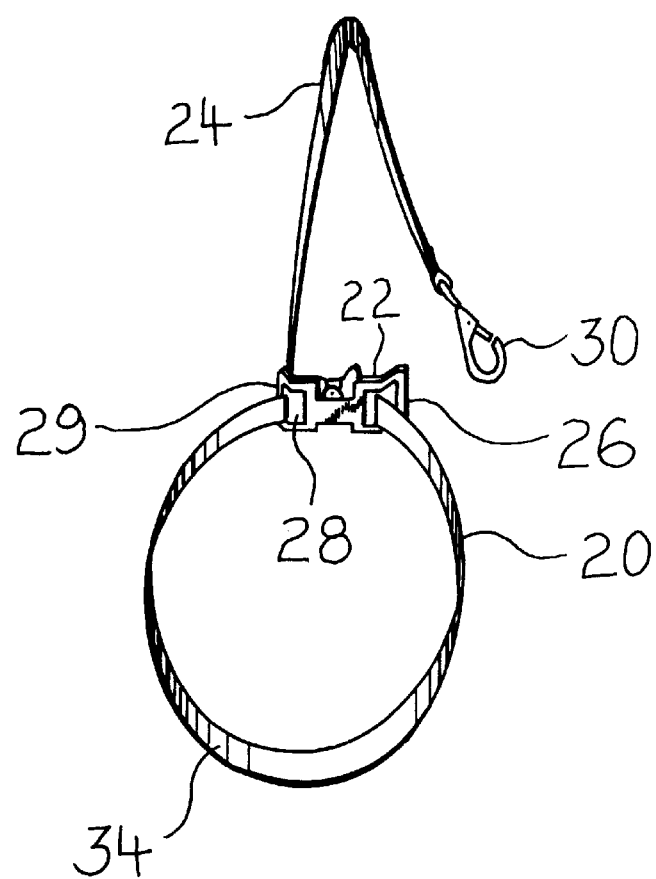
FIG. 4 is a front isometric view of hobble.

Referring now also to FIG. 4, hobble 20 comprises snap hook 30 attached to one extreme of hobble strap 24, and hobble alligator clip 22 attached to an opposite extreme of hobble strap 24. Hobble alligator clip 22 comprises hobble alligator clip back bar 26, hobble alligator clip mouth 28, and (as in belt alligator clip 6) spring-loaded teeth 16 pressing against hobble alligator clip mouth bar 29.

In use, the extreme of hobble strap 24 to which snap hook 30 is attached is threaded through hobble alligator clip mouth 28, thereby forming hobble noose 34. The feet of prisoner 32 are inserted through hobble noose 34, and then hobble noose 34 is tightened around the ankles of prisoner 32 by pulling on the extreme of hobble strap 24 to which snap hook 30 is attached. Spring-loaded teeth 16 clamp down on hobble strap 24 and hold it in place against hobble alligator clip mouth bar 29, thus effectively hobbling prisoner 32.

Figure 5:
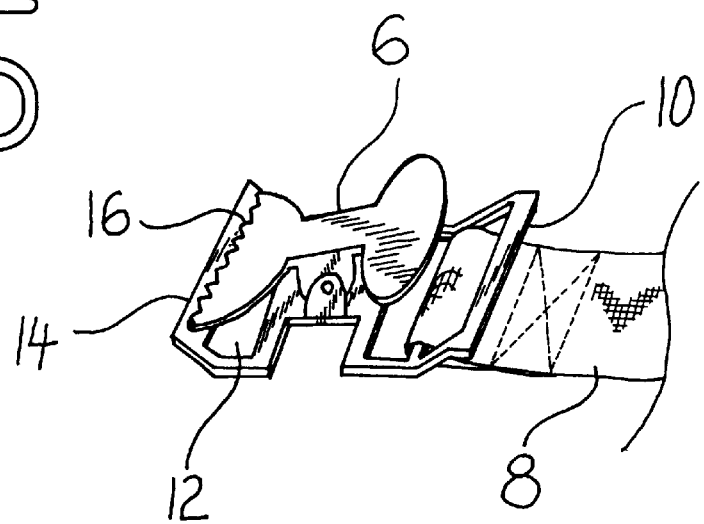
FIG. 5 is a side elevated isometric view of a belt alligator clip.

FIG. 5 is a side elevated isometric view of belt alligator clip 6. Spring-loaded teeth 16 press against belt alligator clip mouth bar 14, thus immobilizing belt strap 8 after it has been threaded through belt alligator clip mouth 12. Belt alligator clip 6 is attached to belt strap 8 as illustrated.

When used to constrain a prisoner, hobble 20 is tightened around the ankles of prisoner 32, belt 4 is tightened around the waist of prisoner 32, and then hobble strap 24 is threaded through belt D-ring 18, snap hook 30 is attached to hobble alligator clip back bar 26, and prisoner 32 is left in a comfortable seated position as is depicted in FIG. 2. In fact, for increased comfort, prisoner 32 can actually lean back against belt 4 (which is constrained against backwards motion by hobble strap 24 attached to hobble 20 around the ankles of prisoner 32), and thus prisoner 32 enjoys the "backrest" effect which the instant invention provides. It is important to note that when prisoner 32 is constrained in the seated position illustrated in FIG. 2 the chances of positional asphyxia occurring are minimized, because prisoner 32 is seated in a conventional, head-up position.

Method of Use:

The instant method for constraining a prisoner in a seated position comprises the steps of:

A. Threading an extreme of hobble strap 24 to which snap hook 30 is attached through hobble alligator clip mouth 28, thereby forming hobble noose 34;

B. Positioning prisoner 32 on his side on the ground;

C. Placing hobble noose 34 around the ankles of prisoner 32, and tightening hobble 20 on the ankles of prisoner 32 by pulling on that portion of hobble strap 24 which extends through hobble alligator clip mouth 28;

D. Placing belt 4 around the waist of prisoner 32 such that belt D-ring 18 is in the general area of the belly button of prisoner 32;

E. Threading an extreme of belt strap 8 opposite belt alligator clip 6 through belt alligator clip mouth 12, and tightening belt 4 around the waist of prisoner 32 by pulling on that portion of belt strap 8 which extends through belt alligator clip mouth 12;

F. Threading the extreme of hobble strap 24 to which snap hook 30 is attached through belt D-ring 18, and fastening snap hook 30 to hobble alligator clip back bar 26; and G. Leaving prisoner 32 in an upright seated position, with his legs resting on the ground in front of him.

In the preferred embodiment, belt strap 8 and hobble strap 24 were made of polypropylene belting, leather, synthetic, wire mesh, or other appropriate organic or synthetic material. In the preferred embodiment, belt D-ring, belt alligator clip 6, hobble alligator clip 22 and snap hook 30 were made of brass, metal, stainless steel, synthetic, plastic, or other appropriate material.

While a preferred embodiment of the invention has been illustrated herein, it is to be understood that changes and variations may be made by those skilled in the art without departing from the spirit of the appending claims.

NOTHING CONTAINED IN THIS DISCLOSURE IS INTENDED TO BE A WARRANTY OR GUARANTEE, EXPRESS OR IMPLIED, REGARDING THE SAFETY OF A PRISONER CONSTRAINED USING THE INSTANT INVENTION.

DRAWING ITEM INDEX 2 apparatus for constraining a prisoner in a seated position
4 belt
6 belt alligator clip
8 belt strap
10 belt alligator clip back bar
12 belt alligator clip mouth
14 belt alligator clip mouth bar
16 spring-loaded teeth
18 belt D-ring
20 hobble
22 hobble alligator clip
24 hobble strap
26 hobble alligator clip back bar
28 hobble alligator clip mouth
29 hobble alligator clip mouth bar
30 snap hook
32 prisoner
34 hobble noose

I claim:

1. An apparatus for constraining a prisoner in a seated position comprising a belt removably attached to a hobble, said belt comprising belt clip means having a belt clip means mouth attached to one extreme of a belt strap and a belt ring attached to said belt strap, said hobble comprising a hobble clip means having a hobble clip means mouth attached to one extreme of a hobble strap and a hook means attached to an opposite extreme of said hobble strap.

2. The apparatus for constraining a prisoner in a seated position of claim 1 wherein said belt ring is sized to admit said hook means and said belt strap, whereby said belt may be removably attached to said hobble by passing an extreme of said hobble strap to which said hook means is attached through said belt ring, and engaging said hook means to said hobble clip means.

3. The apparatus for constraining a prisoner in a seated position of claim 2 wherein said belt clip means is a belt alligator clip comprising a belt alligator clip mouth and spring-loaded teeth pressing against a belt alligator clip mouth bar, whereby said belt may be tightened around a prisoner's waist by threading an extreme of said belt strap opposite said belt alligator clip through said belt alligator clip mouth, and pulling on a portion of said belt strap which extends through said belt alligator clip mouth.

4. The apparatus for constraining a prisoner in a seated position of claim 2 wherein said hobble clip means is a hobble alligator clip comprising a hobble alligator clip mouth and spring-loaded teeth pressing against a hobble alligator clip mouth bar, whereby said hobble may be tightened around a prisoner's ankles by threading an extreme of said hobble strap opposite said hobble alligator clip through said hobble alligator clip mouth, and pulling on a portion of said hobble strap which extends through said hobble alligator clip mouth.

5. The apparatus for constraining a prisoner in a seated position of claim 4 wherein said hook means is a snap hook.

6. The apparatus for constraining a prisoner in a seated position of claim 5 wherein said hobble alligator clip further comprises a hobble alligator clip back bar, and wherein said belt is removably attached to said hobble by engaging said snap hook with said hobble alligator clip back bar.

7. The apparatus for constraining a prisoner in a seated position of claim 2 wherein said belt ring is a belt D-ring.

8. A method for constraining a prisoner in a seated position using an apparatus comprising a belt removably attached to a hobble, said belt comprising a belt clip means having a belt clip means mouth attached to one extreme of a belt strap and a belt ring attached to said belt strap, said hobble comprising a hobble clip means having a hobble clip means mouth attached to one extreme of a hobble strap and a hook means attached to an opposite extreme of said hobble strap, said method comprising the steps of:

A. Threading an extreme of said hobble strap to which said snap means is attached through said hobble clip means mouth, thereby forming a hobble noose;

B. Placing said hobble noose around ankles of a prisoner, and tightening said hobble on the prisoner ankles by pulling on a portion of said hobble strap which extends through said hobble clip means mouth;

C. Placing said belt around a waist of said prisoner such that said belt ring is in the general area of a belly button of said prisoner;

D. Threading an extreme of said belt strap opposite said belt clip means through said belt clip means mouth, and tightening said belt around a waist of said prisoner by pulling on a portion of said belt strap which extends through said belt clip means mouth;

E. Threading an extreme of said hobble strap to which said hook means is attached through said belt ring, and fastening said hook means to said hobble clip means.

9. The method for constraining a prisoner in a seated position of claim 8 comprising a further step of leaving said prisoner in an upright seated position on a surface, with his legs resting on said surface in front of him.

10. The method for constraining a prisoner in a seated position of claim 8 comprising an initial step of positioning said prisoner on his side on a surface.

\* \* \* \* \*